US006576430B1

(12) United States Patent
Hsieh et al.

(10) Patent No.: US 6,576,430 B1
(45) Date of Patent: Jun. 10, 2003

(54) DETECTION OF LIGANDS BY REFRACTIVE SURFACE METHODS

(75) Inventors: Helen V. Hsieh, Durham, NC (US); J. Bruce Pitner, Durham, NC (US); Jason E. Gestwicki, Madison, WI (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/716,566

(22) Filed: Nov. 20, 2000

(51) Int. Cl.[7] ...................... G01N 33/53; G01N 33/543; G01N 21/00; G01J 3/00; G01B 9/00

(52) U.S. Cl. ............................ 435/7.1; 435/6; 435/7.8; 435/7.92; 435/174; 435/287.1; 435/287.2; 435/808; 435/964; 436/86; 436/149; 436/164; 436/173; 436/518; 436/805; 422/68.1; 422/82.05; 422/82.11; 356/51; 356/73; 356/73.1; 356/300; 356/305; 356/311; 356/328; 356/330; 356/337; 356/432; 356/445; 356/450; 356/451; 356/477; 356/517; 356/521; 356/928

(58) Field of Search .......................... 356/51, 73, 73.1, 356/300, 305, 311, 328, 330, 337, 450, 451, 477, 517, 521, 432, 445, 928; 422/68.1, 82.05, 82.11; 435/6, 7.1, 7.8, 7.92, 174, 287.1, 287.2, 288.7, 808, 964; 436/86, 149, 164, 173, 518, 805

(56) References Cited

U.S. PATENT DOCUMENTS

| | | | | | |
|---|---|---|---|---|---|
| 4,931,384 | A | * | 6/1990 | Layton et al. | 435/7 |
| 5,064,619 | A | * | 11/1991 | Finlan | 422/82.05 |
| 5,478,755 | A | * | 12/1995 | Attridge et al. | 436/518 |
| 5,538,850 | A | * | 7/1996 | King et al. | 435/6 |
| 5,573,957 | A | * | 11/1996 | Cardone et al. | 436/518 |
| 5,631,171 | A | * | 5/1997 | Sandstrom et al. | 436/518 |
| 5,641,640 | A | * | 6/1997 | Hanning | 435/7.92 |
| 5,658,732 | A | * | 8/1997 | Ebersole et al. | 435/6 |
| 5,955,377 | A | * | 9/1999 | Maul et al. | 436/518 |
| 5,955,378 | A | * | 9/1999 | Challener | 436/525 |
| 5,965,456 | A | * | 10/1999 | Mamlqvist et al. | 436/514 |
| 6,294,391 | B1 | * | 9/2001 | Badley et al. | 310/311 |
| 6,432,723 | B1 | * | 8/2002 | Plaxco et al. | 436/518 |

FOREIGN PATENT DOCUMENTS

| | | | |
|---|---|---|---|
| WO | WO-97/44664 A1 | * | 11/1997 |
| WO | WO 98/26288 | | 6/1998 |

OTHER PUBLICATIONS

J. Thomson, et al. A thermodynamic study of the binding of linear and cyclic oligosaccharides to the maltodextrin–binding protein of *Escherichia coli*, (1998. Biophysical Chemistry, 70, 101–108).

L. Nieba, et al. BIOCORE Analysis of Histidine–Tagged Proteins Using a Chelating NTA Sensor Chip, (1997. Analytical Biochemistry, 252, 217–228).

T.L. Blair, et al. Fiber Optic for Ca2+ Based on an Induced Change in the Conformation of the Protein Calmodulin (1994. Anal. Chem. 66, 300–302).

T. Ozawa, et al. Metal Ion Selectivity for Formation of the Calmodulin–Metal–Target Peptide Ternary Complex Studied by Surface Plasmon Resonance Spectroscopy (1999. Biochim. Biophys. Acta, 1434, 211–220).

E. Takano, et al. Real–Time Analysis of the Calcium–Dependent Interaction between Calmodulin and a synthetic Oligo Peptide of Calcineurin by a Surface Plasmon Resonance Biosensor (1994. FEBS Lett. 352, 247–250).

M.E. Jones, et al. Bioremediation Monitoring Using Optical Fiber Long Period Grating (LPG)–Based Sensors 2000 (NSF Design and Manuf. Research Conf., Vancouver, Poster No. SBIR–510).

H.V. Hsieh, et al., Measurement of Clostridium Perfringens B–Toxin Production by Surface Plasmon Resonance (1998. Vaccine 16, 997,1003).

S. Boussaad, et al. High–Resolution Multiwavelengh Surface Plasmon Resonance Spectroscopy for Probing Conformational and Electronic Changes in Redox Proteins (2000. Anal. chem. 72,222–226).

H. Sota and Y. Hasegawa, Detection of Conformational Changes in an Immobolized Protein Using Surface Plasmon Resonance (1998. Anal. Chem. 70, 2019–2024).

Z. Salamon, et al. Plasmon Resonance Studies of Agonist/Antagonist Binding to the Human 8–Opioid Receptor: New Structural Insights into Receptor–Ligand Interactions (2000.Biophysical Journal, 79. 2463–2474).

M. Gerstein, et al. Structural Mechanisms for Domain Movements in Proteins (1994. Biochemistry, 33, 6739–6749).

F.A. Quiocho, et al. Atomic structure and specificity of bacterial periplasmic receptors for active transport and chemotaxis: variation of common themes (1996. Molecular Microbiology, 20(1), 17–25).

(List continued on next page.)

*Primary Examiner*—Long V. Le
*Assistant Examiner*—Kartic Padmanabhan
(74) *Attorney, Agent, or Firm*—Jaconda Wagner

(57) ABSTRACT

Methods for detection and analysis of allosteric receptor/ligand binding by changes in surface refractive index are provided. When analyzed by surface plasmon resonance, binding of such allosteric binding agents to their ligands may result in a negative deviation in the optical response (i.e., a decrease in resonance angle) or in an increase in the optical response (i.e., an increase in resonance angle) depending on the binding properties of the selected allosteric receptor. Other methods for analysis of surface refractive index are also useful in the invention. The methods of the invention are particularly useful for small ligands which would not be expected to produce detectable changes in refractive index because they do not add significant mass upon binding.

20 Claims, 5 Drawing Sheets

OTHER PUBLICATIONS

T. Berggard, et al. Ca2+–and H+–Dependent Conformational Changes of Calbindin D28k (2000, Biochemistry, 39, 6864–6873).

A. Di Venere et al. Opposite Effects of Ca2+ and GTP Binding on Tissue Transglutaminase Tertiary Structure (2000. Journal of Biological Chemistry, 275, 3915–3921).

R. Karlsson, et al. Practical aspects concerning direct detection of low molecular weight analytes using BIOCORE 2000, (1997. BIA Journal, special issue, 18–24).

F. Markey, BIOCORE 3000—primed to perfection, (1998. BIA Technology, 2, 4–7).

W.B. Saunders Company, Dorland's Illustrated Medical Dictionary 27th Edition, p. 51.

* cited by examiner

DETECTION OF LIGANDS BY REFRACTIVE SURFACE METHODS

FIELD OF THE INVENTION

The present invention relates to detection of ligand-receptor interactions by monitoring changes in refractive index and in particular to detection of such interactions between relatively small ligands and relatively large receptors.

BACKGROUND OF THE INVENTION

Refractive index is defined as the ratio of the velocity of a specific radiation in a vacuum to its velocity in a given medium. The direction of a ray of light is changed (i.e., refracted) upon passage from one medium to another of different density or when traversing a medium whose density is not uniform. One method of monitoring such refraction is Surface Plasmon Resonance (SPR), which is based upon the phenomenon of total internal reflection, wherein light traveling through a medium of higher refractive index (e.g., glass) is totally internally reflected upon encountering a medium of lower refractive index (e.g., solution) at a sufficiently oblique angle. In SPR detection, the intensity of the reflected light is dampened by the presence of a metal surface at the interface of the two media. The decrease in intensity occurs at a well-defined angle, which is dependent on the refractive indices of the two media, referred to as the "resonance angle". As proteins adsorb onto the metal surface, the refractive index of the solution near the interface changes, shifting the angle at which the reflected light is dampened (i.e, shifting the resonance angle). Detection of the shift in the resonance angle is the basis of an apparatus called the BIACORE™, in which one ligand is immobilized onto a chemically modified gold surface, and the association and dissociation of a soluble ligand to the immobilized ligand is monitored as a function of real time. This optically based sensor allows direct detection of proteins in complex solutions, such as fermentation media (H. V. Hsieh, et al., 1998. Vaccine 16, 997–1003). The signal output of the BIACORE™ is referred to as a resonance unit (RU) and reflects the resonance angle. In general for proteins, 1 RU is approximately 1 pg/mm$^2$. Other instruments for measurement of SPR are available from Bio-Tul (Plasmoon) and Texas Instruments (Spreeta). Other companies developing instruments based on surface refractive index changes include Luna Innovations (Long Period Grating-based sensors, or LPG) and Affinity Sensors (IAsys).

SPR and similar techniques have been used to analyze the binding of ligands and receptors. Because the refractive index of the solution near the solid-liquid interface can be affected by the mass of the molecules at the interface, in general binding of a ligand and receptor increases mass and results in an increase in the angle of reflection. SPR instruments such as the BIACORE™ monitor the binding event continuously. Using these techniques, binding kinetics and affinity can be analyzed.

More recently SPR has been used to study conformational changes in proteins. H. Sota and Y. Hasegawa (1998. Anal. Chem. 70, 2019–2024) immobilized E. coli dihydrofolate reductase and observed an increase in SPR signal with acid denaturation of the protein. S. Boussaad, et al. (2000. Anal. Chem. 72, 222–226) reported the use of SPR to monitor the electronic state of cytochrome c and observed a decrease in resonance angle as the protein was switched from the oxidized to the reduced state, indicating an associated conformational change. These examples, however, do not involve receptor-ligand binding.

One shortcoming of SPR analysis of ligand/receptor interactions is that the change in mass upon binding must be large enough to be detected as a change in refractive index. SPR is typically used for monitoring binding of relatively large ligands to immobilized receptors (e.g., antibody/antigen binding). This binding is accompanied by a relatively large increase in signal because the significant increase in mass of the complex results in a large change in refractive index. Although instruments such as the BIACORE™ are quite sensitive, binding of very small ligands to the surface is typically not detectable because the increase in mass is too small to be detected as an increase in refractive index. An example of a binding reaction which would be expected to be below the detection limits of currently available SPR instruments (based on the minimal increase in mass upon binding) is binding of calcium to calmodulin (CaM). For this reason, alternative assays such as the fluorescence assay described by T. L. Blair, et al. (1994. Anal. Chem. 66,300–302) which do not involve SPR have been used to study conformational changes upon CaM/calcium binding. SPR assays for analysis of CaM binding so far have been limited to systems in which calcium mediates binding of CaM in solution to an immobilized oligopeptide, such as reported by T. Ozawa, et al. (1999. Biochim. Biophys. Acta 1434, 211–220) and E. Takano, et al. (1994. FEBS Lett. 352, 247–250). In these systems the use of CaM (molecular weight) ~17000) as the solution molecule makes the interaction detectable by conventional SPR methods.

Optical fiber long period grating (LPG)-sensors have been used for detection of biological targets by applying affinity coatings to the fiber surface (M. E. Jones, et al. 2000. NSF Design and Manuf. Research Conf., Vancouver, Poster Number SBIR-510). The LPG scatters out light at a particular wavelength based on grating period, fiber refractive index and the refractive index of the surrounding medium. As the affinity coating absorbs the target molecule the refractive index changes and causes a shift in the wavelength of scattered light "seen" by the LPG. The authors report detection of β-galactosidase binding to a ligand-based affinity coating (polyclonal antibodies) as a shift in wavelength, however, such binding produces a relatively large change in mass but does not result in a conformational change in the receptor.

The prior art has not reported the use of surface refractive methods such as these for analysis of ligand binding to allosteric receptors. Although CaM/Ca binding is allosteric, the CaM binding studies described above do not detect it because calcium is bound to CaM prior to binding of the complex to the immobilized oligopeptide. Binding of the complex to the oligopeptide, which is the binding being detected, is not allosteric.

SUMMARY OF THE INVENTION

It has now unexpectedly been found that changes in refractive index can be used to detect binding of ligands to immobilized receptors when the receptor (e.g., a binding protein) or the receptor-surface complex undergoes a conformational change upon binding to the ligand. The conformational change is detectable even when the ligand is small and the receptor is large, which would not be predicted based on the increase in mass upon ligand binding. Unexpectedly, binding of such allosteric binding agents to their ligands may produce negative deviations in the optical response on SPR (i.e., a decrease in resonance angle). While not wishing to be bound by any particular theory of how the invention operates, Applicants believe that the reduction in signal upon binding may be due to the binding protein "closing" or "collapsing" around the ligand as it binds. This could result in a decrease in the hydrodynamic volume which is greater than the increase in mass upon binding. Conversely, an increase in the optical response has been observed on SPR when the allosteric binding agent "opens" upon binding of the ligand. This response may result in an increase in the molecular volume due to a conformational change which is more significant than the added mass of the ligand. However, whether the change in refractive index is positive or negative for any given receptor-ligand pair may depend on the method and instrumentation used to make the determination, as the changes observed on LPG do not always follow those observed on SPR.

The present invention therefore provides a novel optical method for detecting and analyzing binding of allosteric receptors to their ligands. The methods of the invention are particularly useful for small ligands which would not be expected to be detectable by changes in surface refractive index because they do not add significant mass upon binding.

DETAILED DESCRIPTION OF THE INVENTION

Figure 1:
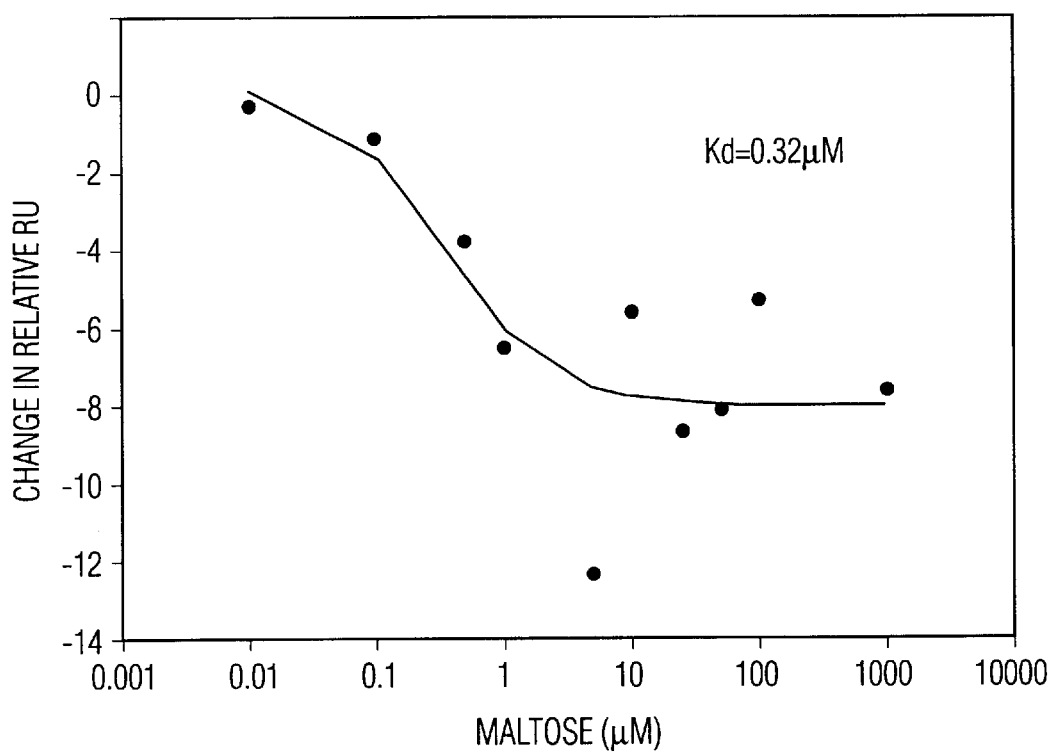
FIG. 1 illustrates the results using the methods of the invention for binding of maltose to MBP, as described in Example 1.

The term "receptor" as used in the art typically refers to the larger of the two binding partners, and it is generally the member of the binding pair which undergoes conformational change upon binding. The "ligand" is typically smaller than the receptor and is bound by the receptor. With respect to SPR assays according to the present invention, it is preferred that the receptor is the immobilized molecule and the ligand is the molecule in solution. This configuration is the opposite of what Biacore recommends. The methods of the invention may be used to detect or analyze the ligand or the ligand-receptor interaction, to analyze binding of the ligand to the receptor, or to analyze the receptor. Typically, detection of ligand-receptor interactions by changes in refractive index depends on the molecular weight (or mass) of the ligand. The larger the ligand the larger the increase in signal upon binding. Small ligand assays using SPR to measure the change in refractive index generally require a very sensitive and expensive instrument such as the BIACORE™ 3000 (approximately $250,000.00) or an indirect assay using a large, competitive binding protein. However, it has now unexpectedly been found that when the receptor undergoes a conformational change upon binding (i.e., when the receptor is allosteric) it is possible to directly detect binding of even a small molecule ligand by changes in refractive index. When analyzed by SPR, a decrease in signal may be observed upon ligand binding to an allosteric receptor, apparently because the receptor closes or collapses upon binding and the hydrodynamic volume of the complex thereby decreases in spite of the added mass of the ligand. Even for small ligands the change in signal is of a magnitude which can be detected by less sensitive and therefore less expensive SPR instruments, and therefore provides an assay which is rapid, inexpensive and can be miniaturized. This is an important improvement because the BIACORE™ 3000 instrument is limited to detecting the binding of molecules which are ≧180 Da when directly monitoring the increase in mass. It therefore typically cannot detect the binding of small molecules such as a calcium ion (40 Da). Using the methods of the present invention any allosteric binding reaction, including binding of calcium to CaM or to transglutaminase, can be detected using simpler and less expensive instrumentation.

Any means known in the art for monitoring changes in refractive index may be used in the methods of the present invention. Preferably, the selected method monitors surface refractive index changes upon receptor-ligand binding, such as SPR or LPG-based methods The receptors of the invention are preferably allosteric, i.e., they change conformation upon binding to the ligand, whether at the binding site itself or elsewhere in the molecule. Typically allosteric binding involves "closing" of the receptor around the ligand, but for some allosteric receptors ligand binding causes "opening" of the receptor conformation. Receptors of this type are often referred to as allosteric receptors or allosteric binding agents and include binding proteins as are well known in the art. Examples of such binding proteins include maltose binding protein (MBP), glucose binding protein (GBP), other proteins which bind small sugars, periplasmic binding proteins, CaM and transglutaminase, however, many other binding proteins with the appropriate properties for use in the invention as described herein are known to those skilled in the art. Additional allosteric receptors, if not already known to be allosteric, may be easily evaluated for use in the invention without the exercise of inventive skill by using the receptor in the methods of the invention and determining whether or not a change in SPR signal is observed upon binding to a small ligand. Such a screening technique will quickly provide information about whether conformational changes are occurring and whether the selected receptor and its ligand can be analyzed using the methods of the invention. The allosteric receptor may be any size, mass or molecular weight but is preferably large relative to the selected ligand so that the change in hydrodynamic volume upon binding is also relatively large. Large allosteric receptors are typically greater than about 15,000 molecular weight, often between about 15,000 molecular weight and about 100,000 molecular weight, but receptors of other molecular weights may be useful in the invention depending on the size of the selected ligand and the extent of the conformational change. Ligands for use in the invention are preferably but not necessarily less than about 1500 molecular weight, more preferably about 30–400 molecular weight, and include amino acids and peptides, nucleotides and oligonucleotides, sugars, ions and other small moieties known in the art. Preferred ligands produce a relatively large change in the conformation of the receptor upon binding. It should be noted that the methods of the present invention do not depend on the absolute relative sizes of the ligand and its receptor. Of more importance is that a selected ligand is small relative to the magnitude of the conformational change in the receptor upon binding. That is, binding of a small ligand to a relatively small receptor may be detected using the methods of the invention if the conformational change in the receptor upon binding is large.

Without intending to limit the scope of the invention, Applicants hypothesize that the change in refractive index signal observed when an allosteric binding agent binds to its ligand may be at least partially due to the associated conformational change in the receptor. That is, a decrease in hydrodynamic volume of the allosteric binding agent or receptor as it "closes" on a ligand may be greater than the change in mass caused by the addition of the ligand. This results in a net decrease in volume of the complex and a net decrease in the refractive index. Similarly, an increase in the refractive index observed for allosteric binding agents which "open" upon binding to their ligands may be due to an increase in hydrodynamic volume which is greater than the added mass of the ligand. This phenomenon has not previously been recognized in studies using refractive index and it was not previously appreciated or expected that the change in refractive index associated with allosteric binding would provide for simple detection of receptor/ligand binding even when the ligand is small.

EXAMPLE 1

MBP was prepared from osmotic shock lysates and coupled to a CM5 (carboxymethyl dextran) chip (BIACORE) using standard EDC/NHS procedures performed with reagents from the BIACORE EDC/NHS coupling kit. MBP was 10 $\mu$M at pH 4.5 in 10 mM NaOAc. Hepes Buffered Saline-EP (HBS-EP: 0.01 M HEPES pH 7.4, 0.15 M NaCl, 3 mM EDTA, 0.005% surfactant P20; BIACORE™ AB) was used as an eluent (O'Shannessy et al., 1992) supplemented with 5 mM $CaCl_2$. Ethanolamine (1.0 M, pH 8.0) was used to quench unreacted esters and was also found to be effective at removing non-covalently adsorbed protein from the chip surface. Maltose solutions were prepared in $dH_2O$ at the desired concentrations. Injections of maltose were 20 $\mu$L at a flow rate of 10 $\mu$L/min (2 minute contact time). Report points were collected at 100 seconds post injection. Report points from injections over a blank surface were subtracted. Data points were discarded for data collected during obvious anomalies, such as air bubbles. Running buffer was HBS-EPA (BIACORE) supplemented with 5 mM $CaCl_2$.

Bound maltose was removed by 20 $\mu$L injection of 100 mM glucose in 10 mM NaOAc pH 4.5. The glucose was recrystallized once from water as the monohydrate to remove possible maltose impurities. After regeneration the surface was allowed to stabilize for 300 seconds before additional ligand injections.

Injection of a maltose solution over the MBP surface resulted in a reproducible net decrease in RUs, in contrast to the positive change in RUs that would have been expected for mass buildup of maltose on the immobilized MBP. A surface bearing 2800 RUs of MBP was used for injection of a series of maltose solutions of varying concentration (FIG. 1). The response to these solutions was measured and an apparent half-maximal response of 0.3 $\mu$M was determined. The dissociation constant (Kd) for maltose binding to MBP in solution has been reported to be approximately 1 $\mu$M (J. Thomson, et al., 1998. Biophys. Chem. 70, 101–108). The similarity of these values suggests a specific ligand-receptor binding event.

EXAMPLE 2

Glucose/Galactose Binding Protein (GGBP) was prepared from osmotic shock lysates and coupled to the CM5 chip surface at 20 $\mu$M at pH 4.5 in 10 mM NaOAc using standard NHS/EDC procedures. Ethanolamine (1.0 M, pH 8.0) was used to quench unreacted esters and was also found to be effective at removing non-covalently adsorbed protein from the chip surface. Buffer flow was maintained overnight to remove additional non-covalently bound GGBP from the surface before ligand injections were performed. A surface bearing 2000 RU of GGBP was used for experiments. Ligands were prepared in $dH_2O$ at the desired concentrations. Injections were 20 $\mu$L at a flow rate of 10 $\mu$L/min (2 minute contact time). Report points were collected at 100 seconds post injection. Report points from injections over a blank surface were subtracted. Typical injections over the blank control surface gave minimal (<5 RU) signals, but were subtracted nonetheless. Ligand injections were repeated 3–5 times and the order of injection was reversed periodically. Data points were discarded for data collected during obvious anomalies, such as air bubbles. Remaining data was subjected to Q tests and error represents single standard deviations. A single set of sugar solutions was used for injection over the control and test surfaces. Running buffer was HBS-EP (BIACORE) supplemented with 5 mM $CaCl_2$. Bound GGBP ligands were removed either by injection of 100 mM $\alpha$-methyl mannoside in 10 mM NaOAc pH 4.5 or by 500–1000 seconds of running buffer wash.

Figure 2:
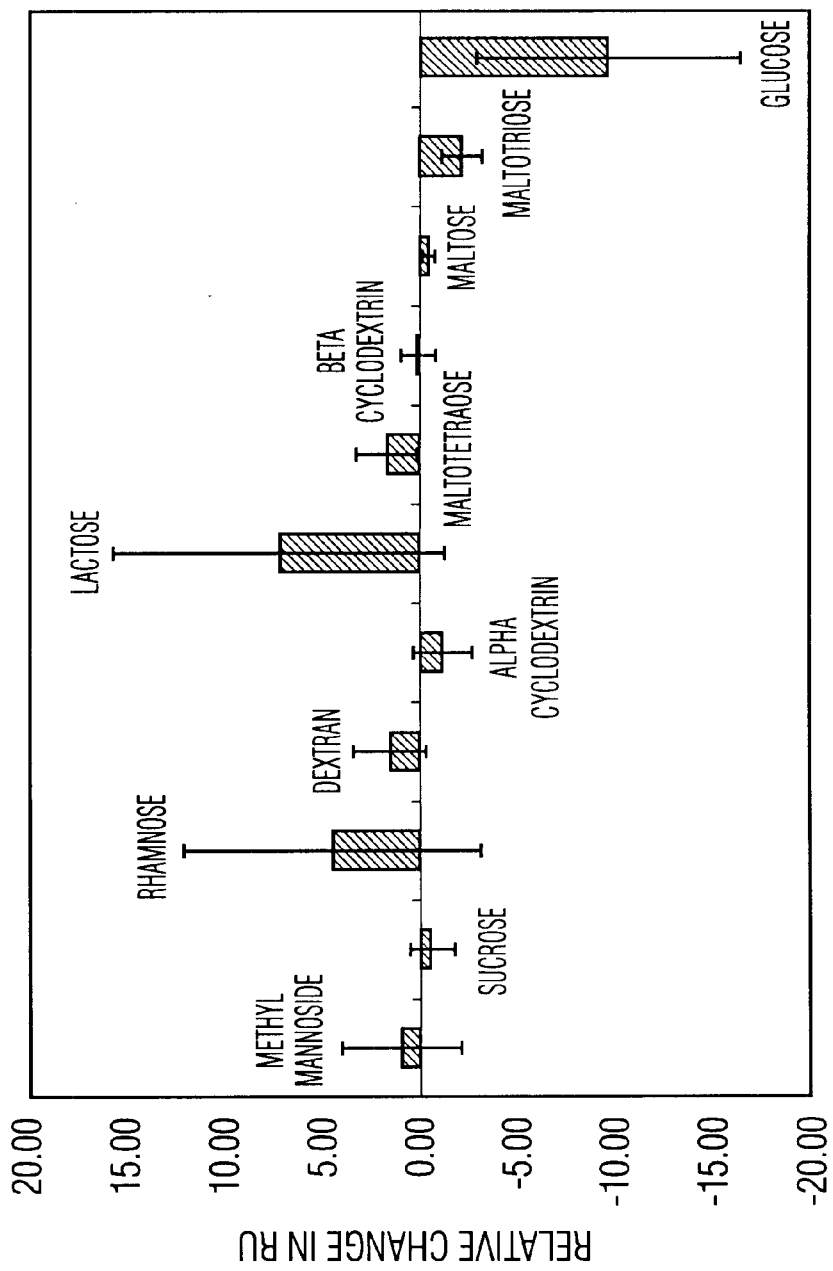
FIG. 2 illustrates the results using the methods of the invention for binding of saccharides to GGBP, as described in Example 2.

A series of saccharides were injected over the GGBP surface (FIG. 2). Only glucose gave a significant negative response in relative RU. Other monosaccharides, disaccharides, and polysaccharides (e.g., maltose, maltotriose, maltotetraose, and cyclodextrins) gave either a negligible or slightly positive increase in relative RU when injected over the GGBP surface. Thus, the SPR surface response is consistent with the specificity of GGBP for glucose found in solution studies. This also demonstrates a method for discriminating non-specific binding events (positive RU response) from specific binding events (negative RU response).

EXAMPLE 3

Tissue transglutaminase (tTG) was obtained from Sigma and prepared at 1.3 mg/mL at pH 4.5 in 10 mM NaOAc. A surface bearing 2500 RU of tTG was prepared using standard EDC/NHS coupling chemistry and was used for all experiments. Ethanolamine (1.0 M, pH 8.0) was used to quench unreacted esters. Calcium chloride was prepared in $dH_2O$ at the desired concentrations. Injections were 20 $\mu$L at a flow rate of 10 $\mu$L/min (2 minute contact time). Report points were collected at 100 seconds post injection. Report points from injections over a blank surface were subtracted. Typical injections over the blank control surface gave minimal (<5 RU) signals, but were subtracted nonetheless. Injections were randomized relative to concentration. Data points were discarded for data collected during obvious anomalies, such as air bubbles. Running buffer was HBS-EP (BIACORE) without calcium supplementation. Calcium was removed from transglutaminase by injection of 5 mM EDTA pH 8.0. After EDTA injection the surface was allowed to stabilize for 300 seconds before additional calcium injections.

Figure 3:
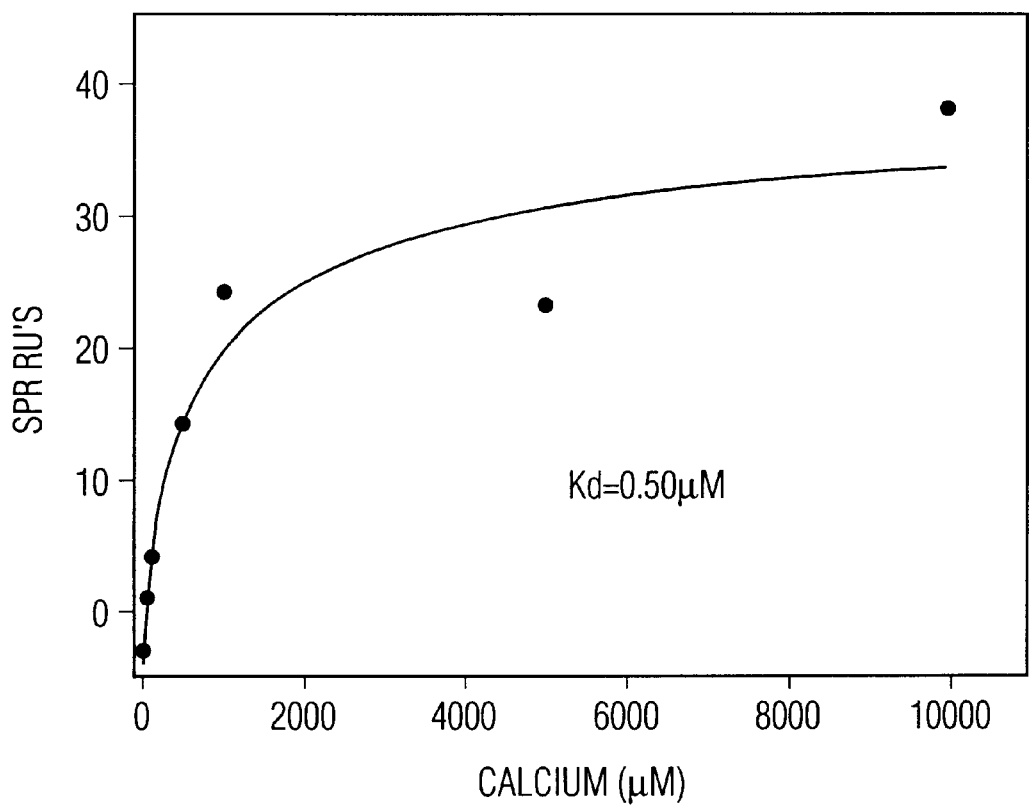
FIG. 3 illustrates the results using the methods of the invention of binding of calcium ions to transglutaminase, as described in Example 3.

Calcium was injected at a range of concentrations. Interestingly, calcium binding to tTG induced a positive change in response (FIG. 3). The half-maximal response of tTG was similar to the reported Kd of calcium for the protein (experimental at 0.5 mM; reported value approximately 1 mM). The detection limit for the ligands on the most recent BIACORE instrument (BIACORE™ 3000) is approximately 180 Da. Therefore, calcium (40 Da) binding is effectively invisible to the instrument. The positive change in response for tTG is consistent, however, with the known conformational change that accompanies ion binding. Whereas MBP, GGBP and CaM are known to "close" on their ligand with a decrease in hydrodynamic radius, tTG undergoes a positive change in hydrodynamic radius upon calcium binding (A. Di Venere, et al., 2000. J. Biol. Chem. 275, 3915–3921).

EXAMPLE 4

Bovine brain calmodulin (CaM) was obtained from Calbiochem and immobilized onto carboxymethyl dextran gold surfaces using standard BIACORE EDC/NHS coupling chemistry. HBS-EP was used as an eluent. CaM was injected at 0.5 mg/mL in 10 mM sodium acetate, pH 4.0 (54 minute injection). This procedure immobilized approximately 480 RU of calmodulin. During the immobilizations, the flow rate was 5 µL/min. For some experiments, the BIACORE™ 3000 was used. For others, a BIACORE™ Upgrade was used. In general, injections were run at a flow rate of 5 or 10 µL/min, in HBP-EP buffer. Varying concentrations of $CaCl_2$ in HBS-EP (3.5–50 mM) were injected on the CaM and blank surfaces. A reduction in signal was observed for all concentrations.

Figure 4:
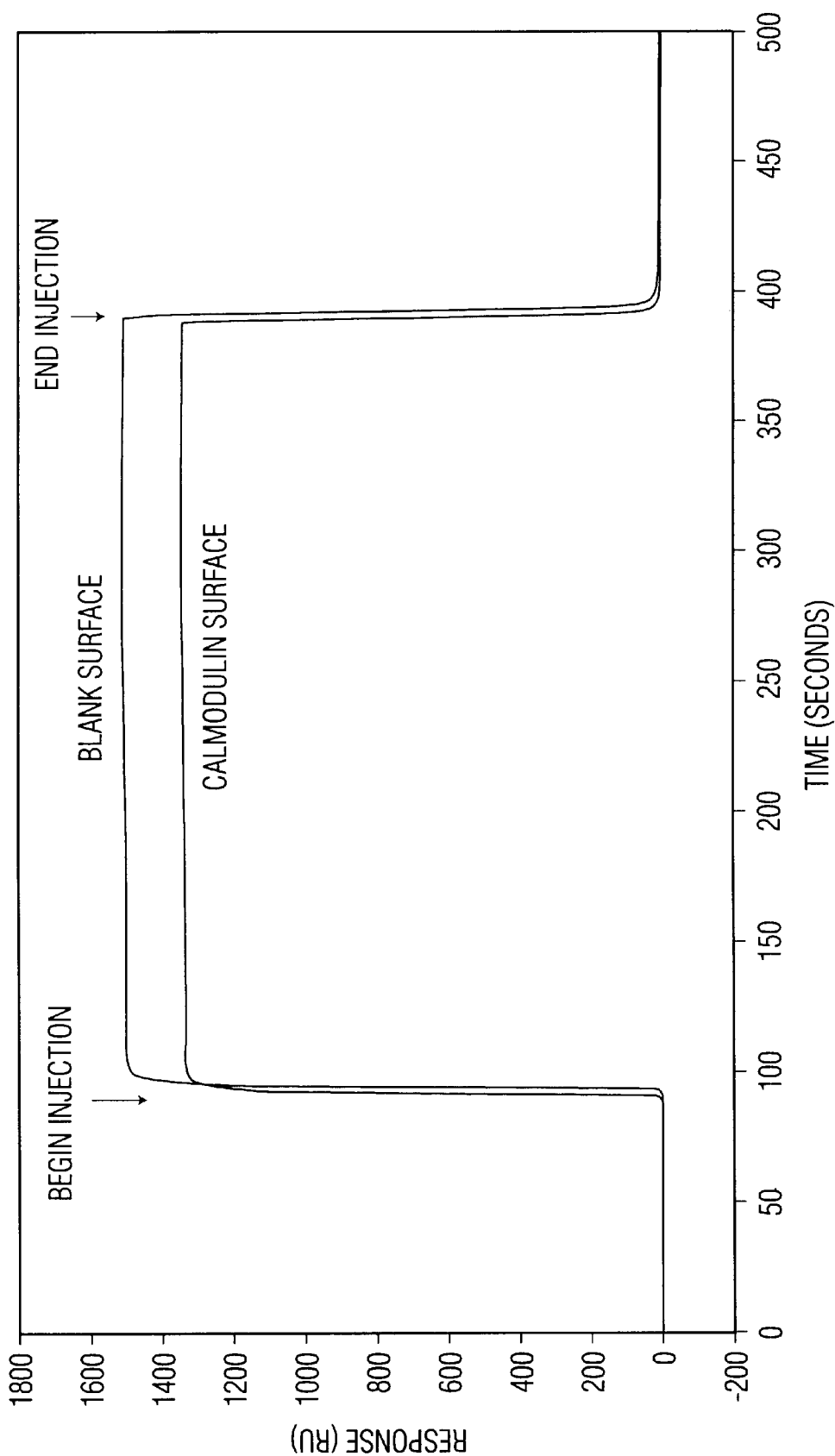
FIG. 4 illustrates the results using the methods of the invention for binding of calcium ions to CaM, as described in Example 4.

The results for 50 mM $CaCl_2$ are illustrated in FIG. 4, showing a decrease in RU upon binding. For both the CaM and blank surfaces the background signal is high and leads to an increase in RU during the injection itself. However, the signal over the blank surface (1502 RU) is much higher than the signal over the CaM surface (1350 RU). For the various concentrations of $CaCl_2$ tested, the magnitude of the response increased with increasing concentration of $CaCl_2$ suggesting that this assay may be used to quantitate the calcium ion.

EXAMPLE 5

LPG fiber sensors with a CMD (carboxymethyl dextran) modified surface were obtained from Luna Innovations, Inc. (Blacksburg, Va.). The fiber surface was activated by incubation of the LPG sensor for one hour with a solution composed of 37 mg/mL EDC and 7.5 mg/mL NHS in 20 mM MES, pH 6.8. The activated sensor was washed with 20 mM MES, pH 6.8, and 10 mM NaOAc pH. 5.0, then transferred to a solution of 20 µM GGBP in 10 mM NaOAc and incubated for two hours at room temperature. After rinsing with 10 mM NaOAc unreacted esters on the sensor surface were inactivated by exposure to a 1M ethanolamine pH 9.0 solution for one hour. Afterward the sensor was rinsed with base buffer (10 mM HEPES, 150 mM NaCl, 0.005% Polysorbate 20, pH 7.4).

Monitoring of the LPG sensor was accomplished through a Lunascan system (Luna Innovations, Inc.) consisting of a spectrometer, detector, controller, laptop computer with interface, and switching mechanism for interrogation of multiple LPG sensors. Comparison to a reference CMD coated LPG sensor not exposed to GGBP indicated about a 0.40 nm wavelength shift of the modified sensor due to the immobilization of protein.

Figure 5:
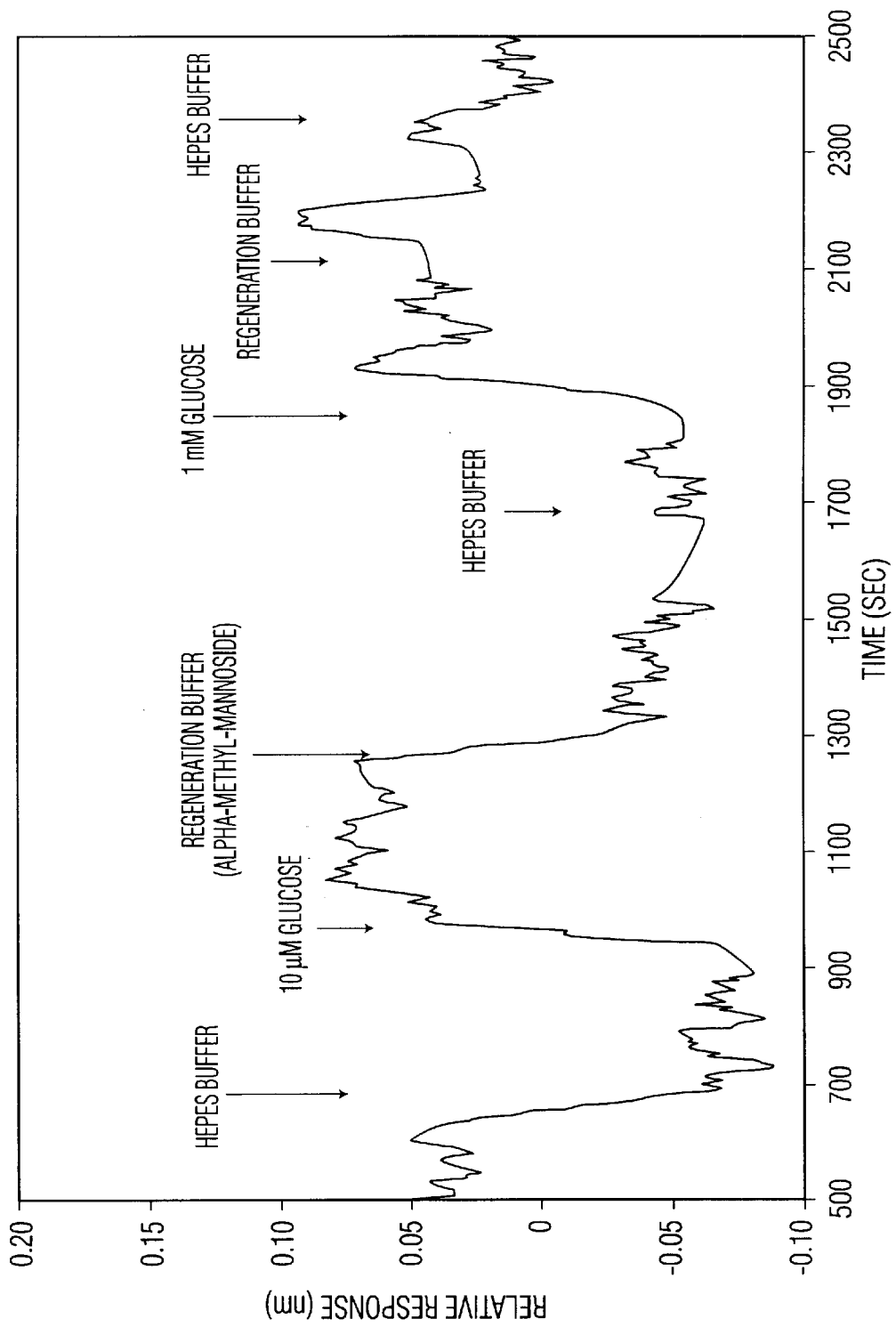
FIG. 5 illustrates the results using the methods of the invention for binding of glucose to GGBP, as described in Example 5.

After thorough rinsing with the HEPES base buffer, the modified sensor and an unmodified reference sensor were exposed to the following solutions (see Table). Between each solution the probes were rinsed with base buffer (HEPES). The trace for the reference channel was subtracted from the GGBP channel to correct for bulk refractive index effects on the sensor performance. The results indicate a detectable and reversible response to glucose levels of 10 µM and 1 mM (FIG. 5).

TABLE

| Reagent Solution | Time (seconds) |
| --- | --- |
| 10 mM HEPES, 150 mM NaCl, 0.005% Polysorbate 20 (v/v), 7.4 | 0 |
| 10 µM Glucose | 950 |
| Regeneration Buffer (α-methyl-mannoside) | 1265 |
| HEPES Buffer | 1700 |
| 1 mM Glucose | 1850 |
| Regeneration Buffer | 2100 |
| HEPES Buffer | 2290 |

The present invention provides methods for detection of small molecules without the need for high molecular weight competitors. It has now been found that binding of receptors that undergo conformational changes to a small ligand may be monitored directly by changes in surface refractive index. Such conformational changes may be used to report on the presence of low molecular weight analytes. Receptors that decrease hydrodynamic volume upon ligand binding (e.g., MBP, GGBP and CaM) produce negative changes in refractive index when analyzed by SPR. Receptors that increase hydrodynamic volume upon ligand binding (e.g., tTG) produce a positive change in refractive index when analyzed by SPR. The positivity or negativity of the response detected upon small ligand binding may vary depending on the method selected for monitoring of the surface refractive index. For example, LPG analysis of GGBP binding to glucose produced a positive response rather than the negative response observed on SPR.

What is claimed is:

1. A method for detecting or analyzing binding of a ligand to an allosteric receptor for said ligand in the absence of high molecular weight competitors or analogues comprising the steps of:

Immobilizing an allosteric receptor that undergoes a conformation change upon binding of a ligand;

Binding a ligand to said immobilized allosteric receptor absent the presence of high molecular competitors or analogues of the ligand; and Detecting the binding of the ligand by measuring a change in surface refractive index, wherein the change in the surface refractive index due to the mass of the ligand is small relative to the change in the surface refractive index due to the conformational change of the immobilized allosteric receptor upon binding of the ligand.

2. The method of claim 1 wherein the receptor is a binding protein.

3. The method of claim 2 wherein the receptor is selected from the group consisting of maltose binding protein, glucose binding protein, calmodulin and transglutaminase.

4. The method of claim 1 wherein the change in surface refractive index is detected by a change in surface resonance properties or by a change in a wavelength of scattered light.

5. The method of claim 4 wherein the change in surface refractive index is detected by surface plasmon resonance or long period grating methods.

6. The method of claim 5 wherein binding is detected by a decrease in resonance angle on surface plasmon resonance.

7. The method of claim 5 wherein binding is detected by an increase in resonance angle on surface plasmon resonance.

8. The method of claim 1 wherein ligand mass is small relative to receptor mass.

9. The method of claim 8 wherein the ligand has a molecular weight of less than 1500.

10. The method of claim 1 wherein the ligand is selected from the group consisting of amino acids, peptides, nucleotides, oligonucleotides, sugars and ions.

11. The method of claim 10 wherein the ligand is maltose, calcium ion or glucose.

12. A method for detecting or analyzing formation of a complex between a ligand and an allosteric receptor for the ligand comprising the steps of:

Immobilizing an allosteric receptor that undergoes a conformation change upon binding of a ligand;

Binding a ligand to said immobilized allosteric receptor absent the presence of high molecular competitors or analogues of the ligand; and Analyzing for the presence of the complex by measuring a change in surface refractive index, wherein the change in the surface refractive index due to the mass of the ligand is small relative to the change in the surface refractive index due to the conformational change of the immobilized allosteric receptor upon binding of the ligand.

13. The method of claim 12 wherein the receptor is a binding protein.

14. The method of claim 12 wherein the receptor is maltose binding protein, glucose binding protein, calmodulin or transglutaminase.

15. The method of claim 13 wherein the presence of the complex is detected by a change in resonance angle on surface plasmon resonance or by a change in a wavelength of scattered light.

16. The method of claim 15 wherein the presence of the complex is detected by a decrease in resonance angle on surface plasmon resonance.

17. The method of claim 12 wherein the ligand mass is small relative to receptor mass.

18. The method of claim 12 wherein the ligand is selected from the group consisting of amino acids, peptides, nucleotides, oligonucleotides, sugars and ions.

19. The method of claim 18 wherein the ligand is maltose, glucose or calcium ion.

20. The method of claim 12 wherein the ligand has a molecular weight of less than 1500.

* * * * *